United States Patent [19]
Korth

[11] Patent Number: 5,346,894
[45] Date of Patent: Sep. 13, 1994

[54] TREATMENT OF LYSO PAF-MEDIATED DISEASES WITH PAF ANTAGONISTS AND PROCEDURE FOR DETERMINING THEIR EFFICACY

[76] Inventor: Ruth Korth, Palestrinastrasse 9, D-8000 München 19, Fed. Rep. of Germany

[21] Appl. No.: 969,674

[22] Filed: Oct. 28, 1992

[30] Foreign Application Priority Data

Nov. 4, 1991 [EP] European Pat. Off. ......... 91118745.8

[51] Int. Cl.$^5$ .................. A61K 31/55; A61K 31/535; A61K 31/44
[52] U.S. Cl. ................................ 514/220; 514/231.2; 514/282
[58] Field of Search ...................... 514/220, 282, 231.2

[56] References Cited

U.S. PATENT DOCUMENTS

| | | | |
|---|---|---|---|
| 4,571,407 | 2/1986 | Chatterjee et al. | 514/464 |
| 4,734,280 | 3/1988 | Braquet | 424/195.1 |

FOREIGN PATENT DOCUMENTS

| | | |
|---|---|---|
| 0151687 | 8/1985 | European Pat. Off. |
| 0256687 | 2/1988 | European Pat. Off. |
| 0459432A1 | 12/1991 | European Pat. Off. |

OTHER PUBLICATIONS

Br. J. Pharmacol., "Interaction of the Paf antagonist WEB 2086 and its hetrazepine analogues with human platelets and endothelial cells", 1989, 98 pp. 653–661.
European Journal of Pharmacology, "Comparison of three paf-acether receptor antagonist ginkgolides", 152 1988, pp. 101–110.

*Primary Examiner*—Marianne M. Cintins
*Assistant Examiner*—T. J. Criares
*Attorney, Agent, or Firm*—Nikaido Marmelstein & Murray & Oram

[57] ABSTRACT

The invention refers to the treatment of lyso-paf-mediated diseases with paf antagonists and a procedure for determining their efficacy. According to the invention for treating a disease caused by lyso paf (1-O-alkyl-sn-glyceryl-3-phosphocholine) as the precursor and metabolit of paf is found in elevated amounts in the liquor of mental and/or inflammatory diseases. Lyso paf regulates via its own receptor the paf receptors on human neutrophils which are then inhibited by paf antagonists. According to the invention for treating a mental and/or inflammatory diseases caused by lyso paf an effective amount of at least one paf antagonist is administered to a subject requiring said treatment, wherein the paf antagonist is a hydrophilic or non-hydrophilic triazolothieno-diazepine or a homologue thereof, a ginkgolide, a ginkgolide mixture or a synthetic ginkgolide derivate, or an analogue of the paf or a mixture with/of these compounds.

1 Claim, 4 Drawing Sheets

TREATMENT OF LYSO PAF-MEDIATED DISEASES WITH PAF ANTAGONISTS AND PROCEDURE FOR DETERMINING THEIR EFFICACY

The invention refers to the treatment and prevention of diseases with paf antagonists mediated by the precursor and metabolite lyso paf and a procedure for determining their efficacy.

The binding of chemotactic factors such as paf-acether (paf, Benveniste et al., J. Exp. Med. 1972, 136: 1356)) to neutrophil surface receptors leads to chemotactic and chemokinetic migration, adherence, degranulation and production of superoxide anions (for review, Malech and Gallin, New Engl. J. Med. 1987, 317,687). Paf is a biologically active etherphospholipid, with the chemical structure 1-O-alkyl-2-acetyl-sn-glycero-3-phosphocholine (Benveniste et al. C. R. Acad. Sci. Paris 1979, 289, 1037; Demoupolos et al., J. Biol. Chem. 1979, 254, 9355). Paf activates human platelets, cultured human endothelial cells and leukocytes via a receptor-dependent mechanism (for review Hwang et al., J. Lipid Med., 1990, 2, 123). Several specific antagonists such as ginkgolides and the hetrazepine WEB 2086 inhibit [$^3$H]paf binding to intact washed human platelets, in close correlation with the inhibitory effect on platelet aggregation (Korth et al., Eur. J. Pharmacol. 1988, 152, 101; Korth et al. Br. J. Pharmacol. 1989, 98, 653) These antagonists also inhibit neutrophil activation suggesting that platelets and neutrophils possesses similar paf binding sites, despite some proposed differences in their signal transduction pathways (Hwang et al. 1988, J. Biol. Chem. 263, 3225).

Neutrophils synthesize paf an acetylation pathway from the precursor lyso paf in response to various stimuli (review in Benveniste J., 1988, Paf-acether, an ether phospholipid with biological activity in Karnovsky, M. L. Leaf and Bolis eds., Progress in Clinical and Biological research. Biological membranes: Aberrations in Membrane Structure and Function vol. 282, p 73, New York, A. R. Liss. Inc.). Paf is metabolized intracellularly to alkyl-acyl-glycero-phosphocholine with lyso paf as an intermediary. In addition, lyso paf is formed via deacetylation of paf by a plasmatic acetylhydrolase and from alkyl-acyl-glycero-phosphocholine by phospholipase $A_2$ activity. Lyso paf was generally considered as an ineffective precursor/metabolite of paf because it does not activate platelets, but here we show for the first time that a lyso paf receptor on neutrophils upregulates the paf receptor and we also show an increase of lyso paf in mental and/or inflammatory diseases. Lyso paf has the chemical structure 1-O-alkyl-sn-glycero-3-phosphocholine, the alkyl being for example hexadecyl or octadecyl.

According to the invention, paf antagonists are used to prevent paf and lyso paf binding to polymorphonuclear neutrophils. As has now been discovered, neutrophils possess beside the paf receptor also a lyso paf receptor which upregulates the paf receptor. It has also been discovered that lyso paf is present in the liquor or mental and/or inflammatory diseases. Thus lyso paf in the liquor should upregulate paf receptors on neutrophils and/or neuronal cells. It is also possible that the increased amount of lyso paf in the liquor leads to an increased adherence and/or emigration of neutrophils to endothelial cells with a damage of the endothelium cell barrier. Since the endothelium provides protection of the brain, various mediators of oedema might then attach the central nervous system.

The substance that inhibits the paf binding sites in this connection can be a triazolo-thieno-diazepine or a homologous compound. In addition ginkgolides and paf analogues, such as CV 3988, have proven suitable. Triazolothieno-diazepines are described in Br. J. Pharmacol. 1987, 90, 139, ginkgolides in "Blood and Vessel" 1985, 16, 558. Of the triazolothieno-diazepine compounds WEB 2086 and WEB 2098 are especially suitable. Of the ginkgolides BN 52020, BN 52021 and a mixture of BN 520202, BN 52021 and BN 52022, which is referred to as BN 52063, achieve the best results. The synthetic compound BN 50739 can also be used.

The chemical term of CV 3988 is rac-3-(N-n-octadecyl carbamoyl oxy)-2-methoxypropyl 2-tiazolioethyl phosphate; the term of WEB 2086 is 3-(4-(2-chlorophenyl)-9-methyl-6H-thieno(3,2-f) (1,2,4)triazolo-(4,3-a)-(1,4) diazepine-2yl)-1-(4-morpholinyl)-1-propanone; the term of WEB 2098 is (3--(4-(2-chlorophenyl)-9-cyclopropyl-6H-thieno(3,2-f)-(1,2,4)triazolo(4,3-a) (1,4)diazepine-2yl)-1-(4-morpholinyl)-1-propanone; the term of BN 52020 is 9H-1, 7a- Epoxymethano)-1H, 6aH-cyclopenta(c)furo(2,3-b)furo(3',2':3,4) cyclopenta (1,2-d) furan-5,9,12 (4H)-trione, 3-tertbutylhexahydro-4, 7b-dihydroxy-8-methyl; the term of BN 52021 is 9H-1, 7a-Epoxymethano)-1H,6aH-cyclopenta(c)furo(2,3-b)furo-(3', 2': 3,4) cyclopenta(1,2-d) furan-5,9,12(4H)- trione, 3 tert-butyl-hexahydro-4, 4b-11-trihydroxy-8-methyl; and the term of BN 52022 is 9H-1, 7a-(Epoxymethano)-1H, 6aH-cyclo-penta(c)furo(3',2':3,4) cyclopenta (1,2-d) furan-5,9,12 (4H)-trione, 3 tert-butyl hexahydro-2,4,7b,11-tetrahydroxy-8-methyl. The chemical term of BN 50739 is tetrahydro-4,7,8,10 methyl (chloro-2 phenyl)-6 (dimethoxy-3,4-phenyl) thio) methylthiocarbonyl-9 pyrido (4',3'-4,5) thieno (3,2-f) triazolo-1,2,4(4,3-a) diazepine-1,4). The paf antagonists can be administered tropically, orally, parenterally or by inhalation. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, emulsions, syrups, suppositories, etc. The effective dose range of the compounds according to the invention includes at least 10 to 500, preferably between 0,1 and 50 mg per dose for intravenous or intramuscular application. It is known to determine the efficacy of paf antagonists by competitive binding tests of the paf and the lyso paf receptor using polymorphonuclear neutrophils. However, a reliable information about the efficacy of paf antagonists is only possible in case of the incubation is performed in the presence and in the absence of lyso paf or by lyso paf binding tests.

In order to conduct a quick and simple test on the effect of lyso paf on paf binding with regard to find paf antagonists in the treatment of lyso paf mediated disease, i.e. mental diseases, the best method is to proceed as follows:

a) lyso paf is measured in the liquor and blood of patients with mental and inflammatory diseases,
b) a given quantity of purified neutrophils is mixed with a given quantity of labeled paf and the antagonist to be determined in the presence of a given quantity of lyso paf, c) a given quantity of the same purified cells is mixed with a given quantity of labeled paf in the presence of a given quantity of lyso paf, d) the cells are separated from the mixtures b) and c) in each case, e) the quantity of labeled paf bound to neutrophils is measured in each case, and f) the efficacy of the paf antagonists is determined from the relationship between the quantity of labeled paf which is bound to the cells according to b) in the presence of the antagonists on one hand, and the quantity of labeled paf which is bound to the cells according to c) in the absence of the antagonist on the other hand.

Preferably, polymorphonuclear neutrophils (PMN) are used as cells for the procedure of the invention for determining the efficacy of paf antagonists. In case PMN are used, they are washed under sterile conditions to avoid PMN activation with an arteficial upregulation of paf receptors. Thereafter the purified cells are preferably dispersed in an isotonic buffer containing delipidated serum albumin, but no calcium ions. In case PMN are used they are concentrated several times before they are used in steps b) and c) in the procedure according to claim 5 in the presence of calcium and magnesium ions. Besides PMN also cell lines can be used to test similar effects on the genetic level.

As labeled ligands tritium-labeled paf, labeled lyso paf, labeled antagonists such as labeled hetrazepines, paf analogues or ginkgolides can be used, for instance. It is also possible to use labeled and unlabeled LA-paf or labeled and unlabeled antibodies against the paf and lyso paf receptors as well as coloured or fluorescence labeled compounds.

The mixing according to steps b) and c) of claim 5 is done preferably at a temperature of 20° C. After mixing, the cells are incubated preferably 30 min. before they are separated according to step d) of the procedure of the present invention. The separation of the cells according to step d) can be performed by filtration or centrifugation.

After this, the quantity of labeled paf which is (specifically) bound to the cells is determined. If radioactively labeled paf is used, only the radioactivity bound to PMN is measured. The radioactivity bound in the filter where there are no cells is subtracted from these values.

By drawing calibration graphs, which are obtained with varying quantities on the antagonist in accordance with step b), it is thus possible to obtain the efficacy of the antagonist at a 50% inhibitory value, i.e. as that quantity of the antagonist which, in relation to a given quantity of cells, leads to a 50% inhibition of the reversible paf binding.

The procedure of the present invention in which lyso paf upregulated paf receptors on PMN are used has been tested successfully particularly with WEB 2086 as a hydrophilic triazolothieno-diazepine. Besides hydrophilic benzodiazepines hydrophobic benzodiazepines can be tested in screening procedure according to the present invention using freshly prepared PMN or cell lines as a model for neuronal cells.

Monoclonal antibodies against lyso paf can be formed for diagnostic tests for the clinical use as the amount of lyso paf increased in mental or inflammatory diseases with upregulation of paf receptors via lyso paf receptors on neutrophils. Although paf was not found in the liquor of patients with mental and cerebral diseases, LA-paf should be tested in the liquor and the serum.

Finally paf receptors are stable for five days in special testing containers and thus the receptor status of blood neutrophils can be investigated in central institutes when blood is taken into special testing containers which are commercial available and which should be modified for smaller blood volumes as proposed in German utility model application G 87 16 004.8.

Since the specific binding of paf or paf-like compounds such as LA-paf (but not lyso paf) is in close correlation with the cellular calcium stream, the procedure of the present invention can also be used for measuring paf or paf like compounds in PMN or PMN-like cell lines by comparing their effect on the cellular calcium stream with calibration graphs of synthetic paf.

BRIEF DESCRIPTION OF THE DRAWING FIGURES

FIG. 1, both A and B, show a plot of [$^3$H] paf binding to neutrophils.

FIG. 2, both A and B, show a plot of [$^3$H] paf binding to neutrophils.

FIG. 4, both A and B, show a plot of cytoplasmic $Ca^{2+}$ flux.

The following examples serve to explain the invention more clearly:

EXAMPLE 1.

Lyso Paf and Paf Isolation Out of the Liquor of Patients with Mental Diseases

Phospholipids were extracted from 48 liquors (500 µl) of patients with mental and inflammatory diseases, analysed for example by HPLC analysis and tested as described (J. Benveniste, C. R. Acad. Science (Paris) 1979, 289, 1037) using aspirinated CP/CPK treated platelets of rabbits. It was found an increased amount of lyso paf in the liquor of patients with psychosis and inflammatory neuronal diseases mainly in the acute phase of multiple sclerosis. No elevated levels of paf were found in the liquor probes. No values for number 7 and 43–48, n=7.

The amount of the paf precursor and metabolite lyso paf is given with coded patient numbers (values are means±s.d. of indicated patient numbers):

Elevated lyso paf level in psychosis:

Nr. 18) Organic psychosis. 3.87 ng/500 µl, 0.043 mg Albumin, 90.0 ng/mg albumin

Nr. 26) Desorientated psychosis. 9.0 ng/500 µl, 0.0875 mg Alb, 102.8 ng/mg albumin Nr. 37) Schizoaffective psychosis. 15.5 ng/500 µl, 0.206 mg albumin, 75.24 ng/mg albumin Nr. 39) DD affective/organ. psychosis, 5.73 ng/500 µl, 0.055 mg albumin, 104 ng/mg albumin Nr. 40) SDAT. 10.5 ng/500 µl, 0.077 mg Alb, 136 ng/mg albumin n=5, x=8.92±4.5 ng lyso paf/500 µl, n=5, x=0.0927±0.06596 mg alb./500 µl, n=5, x=101.61±22.47 ng lyso paf/mg albumin Inflammatory diseases of the central nervous system including multiple sclerosis:

Nr. 5) State after bite of a tick with sudden reduction of the faculty of vision (Gen. not clear, encephalitis?). 3.04 ng/500 µl, 0.0535 mg Alb, 56.82 ng/mg albumin Nr. 21) Unclear virus disease, (for exclusion of inflammatory cerebral disease). 4.41/500 µl, 0.083 mg Alb, 53.13 ng/mg albumin Nr. 30) Unclear inflammatory symptoms of the brain stem, 5.0 ng/500 µl, 0.139 mg Alb, 35.97 ng/mg albumin Nr. 29) Depress. syndrom during multiple sclerosis. 6.25 ng/500 µl, 0.139, 55.30 ng/mg alb.

Nr. 31)Depress. syndrom during multiple sclerosis 8.5 ng/500 µl, 0.0705 mg albumin 120.6 ng/mg albumin Nr. 33) Suspicion in inflammatory cerebral disease, 3.2 ngl/500 µl, 0.062 mg Alb, 51.61 ng/mg albumin Nr. 34) Control after penicillin treatment of a luetic cerebral disease, with meningitis. 3.94 ng/500 µl, 0.01035 mg Alb, 38.06 ng/mg albumin Nr. 36: Suspicion in E.d., 7.5 ng/500 µl, ? mg albumin Nr. 41: Brain atrophy (VII, VIII, IX, XII) and encephalitis. 20.0 ng/500 µl, 0.2985 mg Alb, 67.0 ng/mg albumin $n=9, x=6.87 \pm 5.26$ ng lyso paf/500 µl,
$n=8, x=0.1069$ mg alb./500 µl,
$n=8, x=60.43 \pm 26.38$ ng lyso paf/mg albumin Neoplastic disease:

Nr. 25) Plasmoblastic lymphom, since 3 days Oculomotoriusparesis li. 14.8 ng/500 µl, 0.2295, mg Alb, 61.0 ng/mg albumin Hebephrenia:

Nr. 2) 3.04 ng/500 µl, 0.0535 mg Alb, 56.82 ng/mg albumin

Nr. 3) 3.37 ng/500 µl, 0.0615 mg alb., 54.8 ng/mg albumin

Nr. 17) 4.37 ng/500 µl, 0.132 mg Alb, 33.1 ng/mg albumin $n=3, x=3.59$ ng lyso paf/500 µl,
$n=3, x=0.0823 \pm 0.0432$ mg alb./500 µl,
$n=3, x=48.2 \pm 13.15$ ng lyso paf/mg albumin Paranoid Syndrom:

Nr. 6) V.a. paranoid hallucinatory schizophrenia, DD drug-induced psychosis. 2.17 ng/500 µl, 0.049 mg Alb, 44.3 ng/mg albumin Nr. 11) Paranoid syndrom. 4.37 ng/500 µl, 0.132 mg albumin, 33.11 ng/mg albumin Nr. 14) Discrete paranoid syndrom, for exclusion of an inflammatory cerebral disease. 4.0 ng/500 µl.

Nr. 15) Paranoid syndrom, 3.87 ng/500 µl, 0.0935 mg albumin, 41.39 ng/mg albumin Nr. 35) Fluctuating paranoid symptoms, organic origin. 3.94 ng/500 µl, 0.1035 mg albumin, 38.06 ng/mg albumin $n=5, x=3.66 \pm 0.86$ ng lyso paf/500 µl,
$n=4, x=0.0945 \pm 0.034$ mg alb./500 µl,
$n=4, x=39.215 \pm 4.8$ ng lyso paf/mg albumin Cerebral disorders of different origin:

Nr. 4) Suspicion in Tolora Hunt syndrom left, 2.48 ng/500 µl, 0.089 mg Alb, 27.86 ng/mg albumin Nr. 8) Ophthalmic hospital, 2.37 ng/500 µl, 0.07 mg Alb, 33.85 ng/mg albumin Nr. 9) Compulsion neurosis, 2.35 ng/500 µl, 0.100 mg Alb, 23.5 ng/mg albumin Nr. 13) Unclear muscle atrophy. 3.75 ng/500 µl, 0.081 mg albumin, 46.29 ng/mg albumin Nr. 19) Choreal syndrom with Dyskenisie. 4.62 ng/500 µl, 0.0645 mg albumin, 71.62 ng/mg albumin Nr. 22) Opticus atrophy. 4.62 ng/500 µl, 0.0555 mg Alb, 83.24 ng/mg albumin Nr. 23) Opticus atrophy, 3.87 ng/500 µl, 0.0745 mg albumin, 51.95 ng/mg albumin Nr. 24) For exclusion of organic brain disease. 3.395 ng/500 µl, 0.1075 mg Alb, 31.58 ng/mg albumin $n=8, x=3.43 \pm 0.95$ ng lyso paf/500 µl,
$n=8, x=0.07913$ mg alb./500 µl,
$n=8, x=46.23 \pm 21.6$ ng lyso paf/mg albumin Without clinical statements:

Nr. 12) 1.8 ng/500 µl, 0.0575 mg Alb, 31.3 ng/mg albumin

Nr. 27) 3.94 ng/500 µl, 0.1355 mg albumin, 29.08 ng/mg albumin

Nr. 28) 2.875 ng/500 µl, 0.1645 mg Alb, 17.48 ng/mg albumin $n=3, x=2.87 \pm 1.0$ ng/500 µl,
$n=3, x=0.125 \pm 0.004$ mg alb./500 µl,
$n=3, x=25.9 \pm 95$ ng lyso paf/mg albumin

EXAMPLE 2

Paf and Lyso Paf receptors and Regulation of Paf Receptors on Human Neutrophils by Lyso Paf.

Key words: Paf-acether, lyso-paf, paf-acether receptors, human neutrophils, $[Ca^{2+}]i$ rise, paf-acether antagonists.

2.1. Preparation of neutrophils.

Neutrophils were prepared according to method described by Boyum (J. Clin. Lab. Invest. Suppl. 1968, 97,77) with some modifications. Briefly, venous blood (40 ml) from normal donors, anticoagulated with citric acid dextrose (7:1, v/v) was sedimented for 30 to 45 min in gelatin 0.3% final (Plasmagel ®). Twenty ml of supernatant were layered on 10 ml Ficoll Hypaque (d=1.077) and centrifuged (400×g, 20 min, 20° C.). The cell pellet containing neutrophils (95%) was resuspended in 500 µl Tyrode's buffer (pH=7.4). Erythrocyte lysis was performed by adding 3 volumes of distilled water for 40 sec, followed by 1 volume NaCl (3.5%, w/v). PMN were then washed twice in Tyrode's buffer (centrifugation at 370×g at 20° C. for 10 min). Cell concentration was adjusted to $5 \times 10^7$ per ml.

2.2. Binding studies.

Binding studies were performed as described by Korth et al. (Thrombos. Res. 1986, 41, 699). PMN ($2.5 \times 10^6$) suspended in 500 µl Tyrode's buffer supplemented with 1.3 mM $CaCl_2$, 1 mM $MgCl_2$ and 0.25% (v/v) fatty acid-free bovine serum albumin (BSA, w/v) were incubated with [$^3$H]paf (0.325–6.5 nM) either for 30 min at 20° C. or for 20 hrs at 4° C. Non-specific binding was assessed with the unlabeled ligands either paf (500 nM) or the specific paf receptor antagonist WEB 2086 (1 µM). In a second set of experiments, [$^3$H]paf binding was performed by adding 3.25 nM [$^3$H]paf to PMN, simultaneously with low dose (5 to 50 nM) of paf, lyso paf, the enantiomer of paf or 2-lyso phosphatidylcholine (LPC) for 30 min at 20° C. [$^3$H]paf binding was also measured in the presence of the phorbol ester 4-phorbol-12-myristate-13-acetate (PMA, 1 to 16 nM) either added simultaneously with [$^3$H]paf or preincubated 15 min at 37° C. previously. The binding of [$^3$H]lyso paf (0.325–0.5 nM) was measured after 30 min incubation at 20° C. in the absence or presence of an excess of unlabeled lyso paf, paf (500 nM) or WEB 2086 (1µM). The effect of low dose paf (5 nM) on the binding of [$^3$H]lyso paf was also investigated.

After the binding procedure, PMN were separated from their suspending medium by filtration in a millipore vacuum system with GF/C filters. Filters were washed with 10 ml Tyrode's buffer at 4° C. and radioactivity was assessed by scintillation. Cell-bound radioactivity on the filters after subtraction of blanks (filter-bound radioactivity in the absence of cells) was expressed in fmol [$^3$H]paf bound per $2.5 \times 10^6$ PMN.

2.3. Measurement of cytosolic free calcium.

The concentration of cytosolic free calcium [$Ca^{2+}$]i was measured using the [$Ca^{2+}$]i indicator fura-2-acetoxymethyl ester (fura-2) as described by Grynkiewicz et al. (J. Biol. Chem. 1985, 260, 3440). After osmotic lysis of erythrocytes, PMN were washed once, resuspended ($2 \times 10^7$/ml) in Tyrode's buffer containing 0.25% BSA, the incubated for 30 min at 37 C. with 2.5 μM fura-2 and washed twice thereafter. They were resuspended ($1 \times 10^6$/ml) in Tyrode's buffer (0.25% BSA) containing either 1.3 mM $CaCl_2$ or 2 mM EGTA and fluorescence changes were monitored using a spectrofluorophotometer Shimadzu RF-500 (Kyoto, Japan) after addition of paf and/or lyso paf (1–100 nM). Cytoplasmic calcium flux was also measured in PMN preincubated with 1 μM WEB 2086 for 3 min before addition of 1 to 500 nM paf. The spectrofluorophotometer was programmed to shuttle between the two excitation wavelengths of 340 and 380 nm every 5 sec while keeping the emission wavelength of 505 nm. The addition of paf produced reciprocal changes (ratios, R) in the fluorescence recorded at two wavelengths, from which [$Ca^{2+}$]i can be calculated. The maximal ratio ($R_{max}$) was obtained by adding 15 μl digitonin (4 μM) and the minimal ratio ($R_{min}$) by adding 37.5 μl EGTA (5 mM). Background values were subtracted from all data. The intracellular $Ca^{2+}$ was calculated with the formula [$Ca^{2+}$]i $= k \times R - R_{min}/R_{max} - R$. K is KD of the fura-2 multiplied with the quotient of the fluorescence at 380 nm from the minimal and the maximal [$Ca^{2+}$]i fluorescence.

2.4. [$^3$H]paf metabolism.

PMN ($2.5 \times 10^6$/500 μl Tyrode's) were incubated as described above (30 min, 20° C., 0.25% BSA) with [$^3$H]paf (0.65 to 6.5 nM) or [$^3$H]lyso paf (3.25 nM), in the absence or presence of 5 nM unlabeled paf or 1 μM WEB 2086. Cells were then separated from the suspending medium by vacuum filtration and phospholipids were extracted as described (Bligh and Dyer, Can. J. Biochem Physiol. 1959, 37, 911) with slight modifications. Briefly, filters were placed in 500 μl water. Dichloromethane/methanol (1:2, v/v) was then added overnight at 4° C., before addition of water containing 2% (v/v) acetic acid. Organic phases were collected and aqueous phases were washed three times with 1 v dichloromethane. High pressure liquid chromatography (HPLC) was performed as described (Benveniste et al. 1979, C.R. Acad. Sci. Paris 289, 1037). The radioactivity was measured in the fractions after subtraction of the background values. Appropriate synthetic markers were used to define the retention time of alkyl-acyl-glycerophosphocholine (alkyl-acyl-GPC) as 11–13 min, paf as 8–25 min and lyso paf 28–33 min.

2.5. Materials.

Tyrode's buffer was composed of (in mM) NaCl, 137; KCl, 2.68; $NaCO_3$, 11.9; $MgCl_2$, 1.0; $NaH_2PO_4$, 0.41; dextrose, 0.5; HEPES 5.0. The following reagents were used: ACD composed of citric acid (0.8%), trisodic citrate (2.2%) and glucose (2.45%); citric acid (0.15M) (all from Merck-Darmstadt, Germany). Fatty acid-free bovine serum albumin (BSA, fraction V) and phorbol-12-myristate-13-acetate (PMA) were from Sigma (St. Louis, Mo. U.S.A.). Radiolabeled synthetic paf-acether ([$^3$H]paf, 1-O-[$^3$H]-octadecyl-2-acetyl-sn-glycero-3-phosphocholine, 80 Ci/mmol) and labeled lyso-paf ([$^3$H]lyso-paf, [$^3$H]paf, 1-O-[$^3$H]-octadecyl-sn-glycero-3-phosphocholine, 150 Ci/mmol) as well as PCS and OCS scintillation fluid were from Amersham (Amersham, U.K.) and were dissolved in pure ethanol. Unlabeled synthetic paf (1-octadecyl-2-acetyl-sn-glycero-3-phosphocholine) and its enantiomer as well as lyso paf (1-octadecyl-sn-glycero-3-phosphocholine) and 2-lyso phosphocholine (LPC) were from Bachem, (Bubendorf, Switzerland) and solubilized in ethanol. WEB 2086 was solubilized in water with 0.1N HCL ultrasonically every day. Whatman GF/C filters were from Ferriére, France. The Millipore vacuum system was from Molsheim and Fura-2-AM from Calbiochem (Germany).

2.6. Results 2.6.1. [$^3$H]paf binding to neutrophils.

Figure 1A:
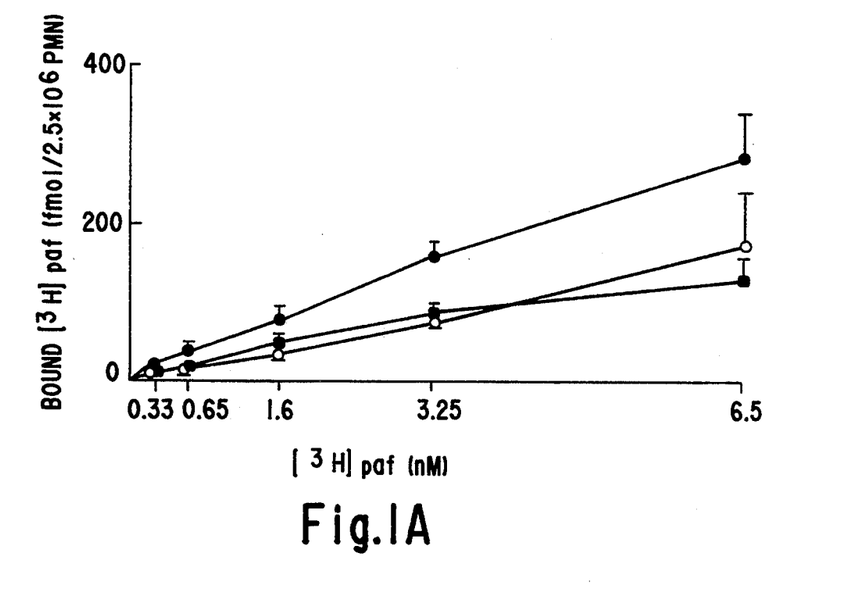
Figure 1B:
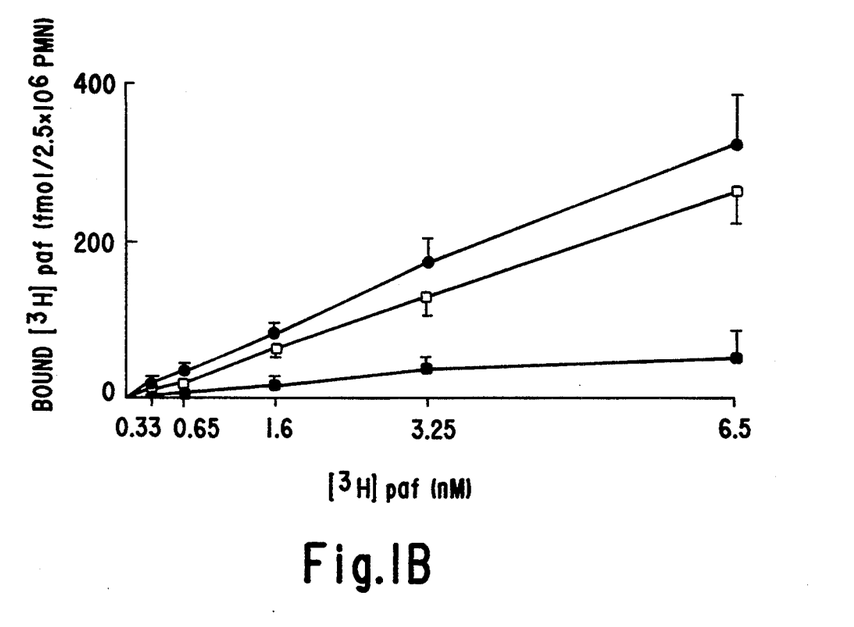
Figure 2A:
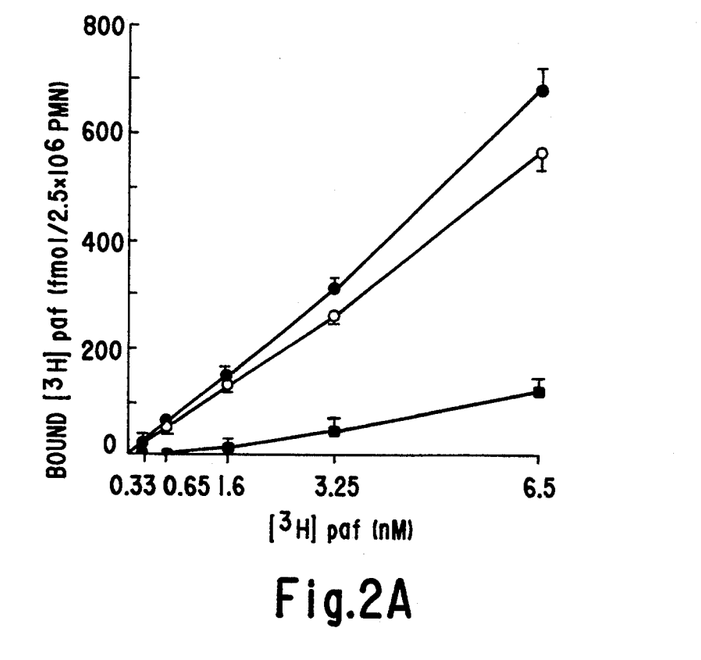
Figure 2B:
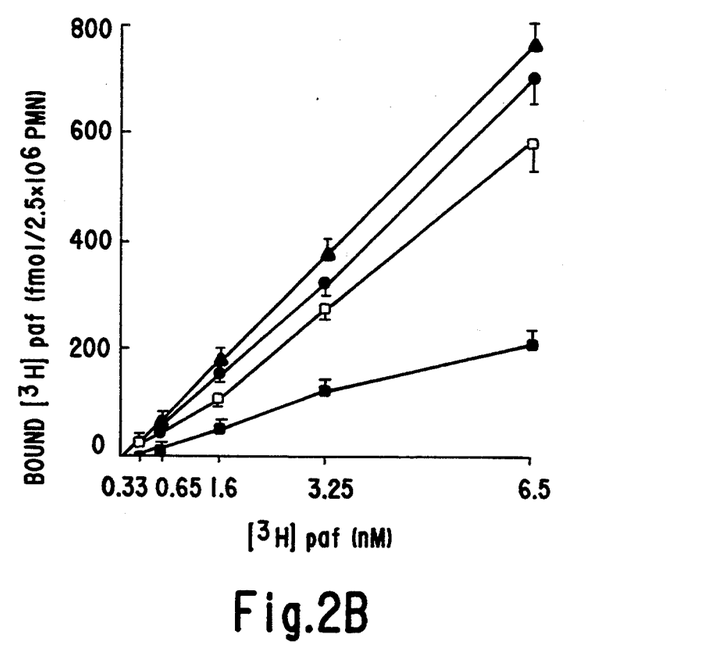

PMN incubated at 4° C. for 20 hours with [$^3$H]paf bound the radioligand in a concentration-dependent manner (FIG. 1 A, B). When used at high concentrations, unlabeled paf (500 nM) or the paf receptor antagonist WEB 2086 (1 μM) inhibited [$^3$H]paf binding. The total binding of [$^3$H]paf (FIG. 1 and 2) was higher at 20° C. vs. 4° C. ($310.5 \pm 13.0$ vs $157.0 \pm 27.4$ fmol per $2.5 \times 10^6$ cells) and reached plateau values after 30 min incubation at 20° C. and 20 hrs at 4° C. (not shown). However, whereas at 4° C. The specific binding reached a plateau at concentrations higher than 3.25 nM added [$^3$H]paf (FIG. 1), it remained unsaturated at 20° C. up to 6.5 nM [$^3$H]paf (FIG. 2).

2.6.2. Effect of paf, lyso paf or structurally-related compounds.

As specific paf binding remained unsaturated at 20° C. up to 6.5 nM [$^3$H]paf, we hypothesized a self triggering effect of low ligand concentrations. Indeed, the total binding of [$^3$H]paf to PMN was significantly increased in the presence of 5 nM unlabeled paf ($p<0.001$, Student's t test for paired samples, $N=6$, FIG. 2 B and Table 1). This increase was inhibited in the presence of WEB 2086 ($p<0.001$, $n=6$). Lyso-paf (5 nM) also increased the [$^3$H]paf binding (table 1, $p<0.001$, $n=6$). This phenomenon was quite certainly linked to paf receptors, because it was inhibited by WEB 2086 (1 μM). The effects of paf or lyso paf were maximal at 5 nM for 30 min incubation and were increased neither with higher concentrations nor with longer incubation periods of up to 2 hrs (not shown). No additive effects on the [$^3$H]paf binding to PMN were observed when paf and lyso paf at low concentration were incubated together (not shown), suggesting that the common either group in the sn-1 position of both molecules is critical for this receptor upregulation. This was further evidenced ;by the fact that neither the paf enantiomer nor the ester group in the sn-1 position of LPC showed an upregulatory effect on [$^3$H]paf binding (table 1).

2.6.3. [$^3$H]lyso paf binding to neutrophils.

Figure 3:
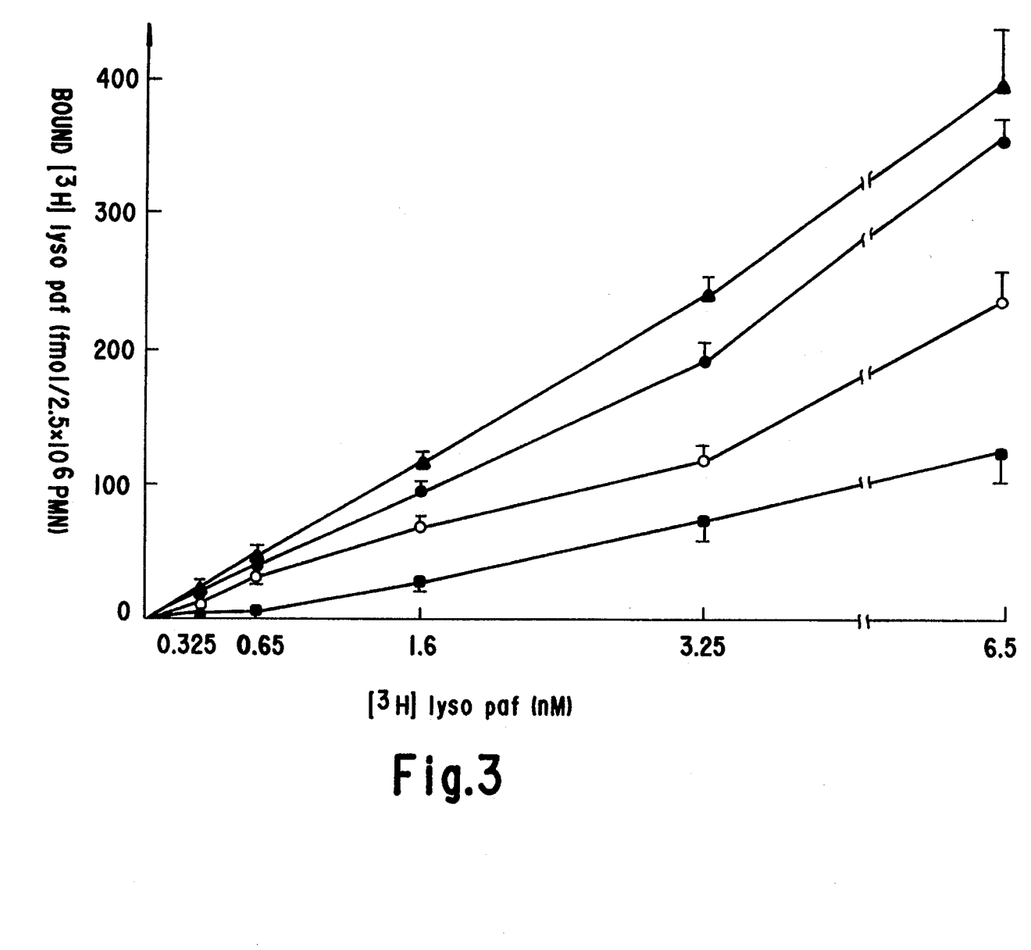
FIG. 3 is a plot of [$^3$H] lyso paf binding to neutrophils.

To strengthen the hypothesis that there are binding sites for paf and lyso paf in the neutrophil membrane, we investigated the [$^3$H]lyso paf binding. As well as binding [$^3$H]paf, PMN bound [$^3$H]lyso paf in a concentration-dependent manner at 20° C., but neither paf (500 nM) (FIG. 3) nor the paf receptor antagonist WEB 2086 inhibited labeled lyso paf binding (not shown). In contrast, the [$^3$H]lyso paf binding increased in the presence of 500 nM labeled paf (FIG. 3). This prompted us to confirm whether low concentrations of paf could have the same effect. Indeed, paf (5 nM) increased the binding of 3.25 nM [$^3$H]lyso paf from $197.0 \pm 4.5$ to $255.0 \pm 10.5$ fmol per $2.5 \times 20^6$ PMN ($n=3$). The latter increase was prevented by the paf receptor antagonist WEB 2086 (1 μM, 212.0±6.4 fmol/2.5×10⁶ PMN), indicating that upregulation of lyso paf binding sites is a paf receptor-dependent process. Unlabeled lyso paf inhibited [$^3$H]lyso paf binding, although this inhibitory effect did not reach saturation at 20° C. (but at 4° C., not shown). These results might indicate two binding sites, the first with the ability to bind the either group present in paf and lyso paf with a upregulatory potency, the second one with the ability to bind the acetyl group of paf.

2.6.4. Cytoplasmic $Ca^{2+}$ flux.

Figure 4A:
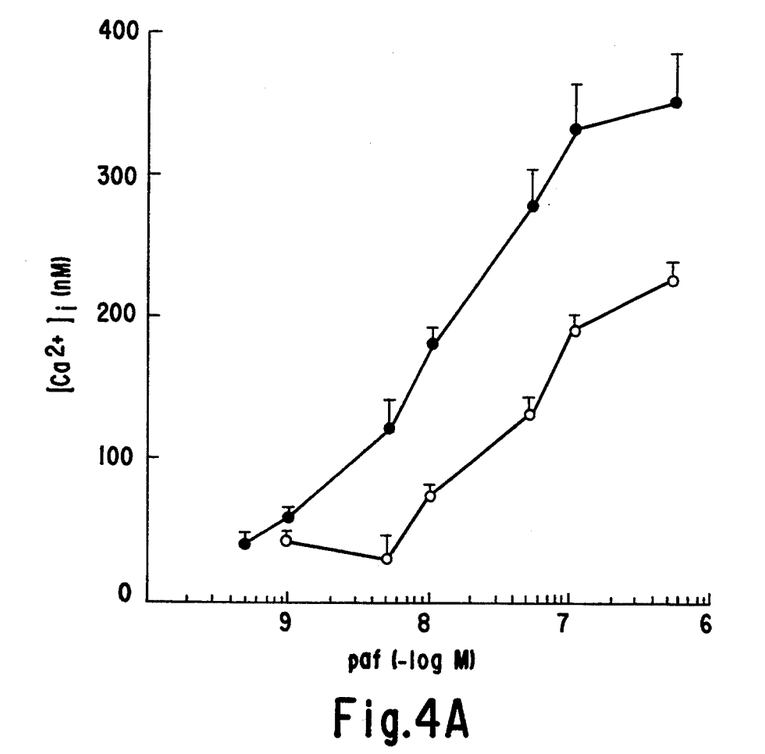
Figure 4B:
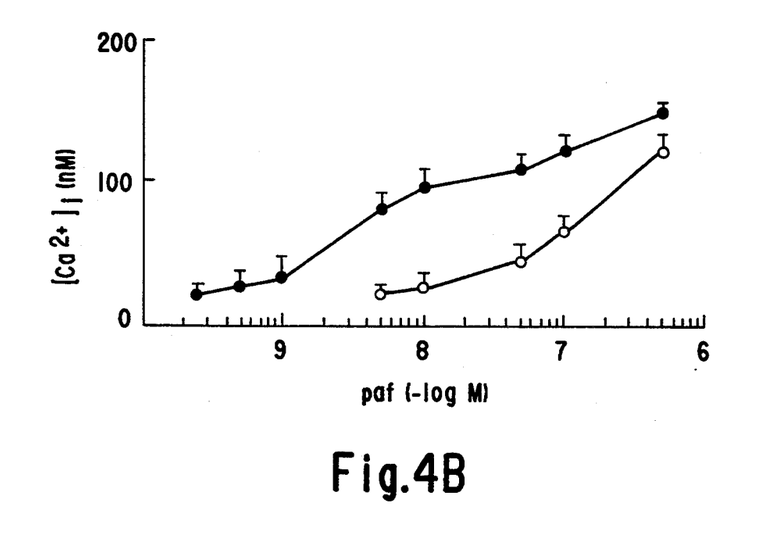

In an attempt to investigate whether paf and lyso paf binding sites are causatively involved in the cellular $Ca^{2+}$ flux, we measured the cytoplasmic $Ca^{2+}$ changes in response to paf in comparison with lyso paf. Addition of paf (1 to 500 mM) to fura-2 loaded neutrophils in the presence of extracellular $CaCl_2$ (1.3 mM) induced a concentration-dependent entry of $Ca^{2+}$ (FIG. 4 A). PMN preincubation (3 min) with WEB 2086 (1 μM) shifted to the right the paf dose-response curve, although decrease of the maximal response indicated some additional inhibition of the $Ca^{2+}$ entry. Similarly, when PMN were suspended in a medium devoid of $CaCl_2$ in the presence of EGTA (2 mM), paf induced the cytosolic mobilization of $Ca^{2+}$ from internal pools (FIG. 4 B). WEB 2086 inhibited the paf-mediated $[Ca^{2+}]i$ rise competitively as it shifted to the right the paf dose-response curve in a parallel manner.

In contrast, lyso paf induced neither $[Ca^{2+}]i$ entry nor mobilization (not shown). Even when PMN were incubated with 5 nM paf together with increasing concentrations of lyso paf, no additional increase of $[Ca^{2+}]i$ could be observed. These results shown the requirement of the acetyl group in sn-2 position of paf for the receptor-dependent $[Ca^{2+}]i$ mobilization in PMN.

2.6.5. Effect of PKC activation on paf binding.

We suspected a role of PKC in the upregulation of paf binding sites induced by low ligand concentrations. Indeed, a dual effect of the PKC activator PMA, depending just as the effect of paf, on its concentration, was observed (table 2). Low concentration of PMA (1 nM) increased [$^3$H]paf binding, at a level similar to that of 5 nM paf, and a higher concentration (16 nM) was inhibitory. Preincubation of PMN with PMA for 15 min at 37° C. enhanced the dual PMA effect with upregulation at low and downregulation at high concentrations, whereas pretreatment with low dose paf desensitized PMN against a second paf challenge and thus failed to upregulate paf receptors.

2.6.6. Paf metabolism.

The metabolism of [$^3$H]paf to alkyl-acyl-GPC and lyso paf as an intermediary was shown under binding conditions (table 3).

2.7. Legends and tables.

FIG. 1: [$^3$H]paf binding to intact human PMN at 4° C.

Neutrophils (2.5×10⁶ per 500 μl) were incubated in the presence of [$^3$H]paf concentrations as shown for 20 hrs at 4° C. before vacuum filtration. Non-specific binding was assessed with 500 nM unlabeled paf (A, ○) or the specific paf receptor antagonist 1 μM WEB 2986 (B, □). The specific binding (■) was calculated as total (●) minus non-specific binding. Values are means±1 s.d. of 3 experiments. FIG. 1 shows the inhibitory effect of WEB 2086 on [$^3$H]paf binding to washed human neutrophils.

FIG. 2: [$^3$H]paf binding to intact human PMN at 20° C.

Neutrophils (2.5×10⁶ per 500 μl) were incubated in the presence of [$^3$H]paf concentrations as shown for 30 min at 20° C. The non-specific binding was assessed either with unlabeled paf (A, ○) or the specific paf receptor antagonist WEB 2086 (B, □). The specific [$^3$H]paf binding (■) was calculated from total [$^3$H]paf binding (A, ●) or that in the presence of 5 nM unlabeled paf (B, ■) minus non-specific binding. Results are means±SEM of 6 experiments. Increase of total [$^3$H]paf binding (B: 3.25 nM) was significant using the "Students t test" (p<0.001). FIG. 2 shows a homologous upregulation of specific [$^3$H]paf binding by submaximal paf concentration.

FIG. 3: [$^3$H]lyso paf binding to human PMN at 20° C.

PMN (2.5×10⁶ per 500 μl) were incubated with the concentrations of [$^3$H]lyso paf as shown and the non-specific [$^3$H]lyso paf binding was assessed with unlabeled lyso paf (500 nM) before vacuum filtration after 30 min incubation period. The total [$^3$H]lyso paf binding (●) increased in the presence of unlabeled paf (500 nM, □). The non-specific lyso paf binding (○) was assessed with excess unlabeled lyso paf (500 nM) and the difference between total and non-specific binding was calculated (■). Results are means±SEM of 3 experiments. FIG. 3 shows the neutrophil receptor for lyso paf and its upregulation [$^3$H]lyso paf binding by paf.

FIG. 4: Paf dose response curve of the cytosolic $Ca^{2+}$ flux.

PMN (10⁶ per ml) were incubated for 3 min at 37° C. under stirring with WEB 2086 (○) or vehicle (●) before paf was added at the concentrations as shown in the presence of 1.3 mM $CaCl_2$ (A) or in the same buffer devoid of $CaCl_2$, containing 2 mM EGTA (B). Means±1 s. d. are of 3 experiments. FIG. 4 shows that neutrophil paf receptors are functionally relevant.

TABLE 1

| | Increase of [$^3$H]paf binding in the presence of different phospholipids. | | | | | |
|---|---|---|---|---|---|---|
| Add. (nM) | paf | paf + WEB | lyso paf | lyso paf + WEB | enantio-paf | LPC |
| 0 | 318 ± 15 | | | | 348 ± 17 | 348 ± 17 |
| 5 | 376 ± 21* | 258 ± 19* | 354 ± 20* | 257 ± 19* | 345 ± 32 | 322 ± 22 |
| 10 | | | 346 ± 20* | 243 ± 16* | 343 ± 29 | 310 ± 19 |
| 50 | | | 342 ± 19* | 240 ± 18* | 325 ± 25 | 311 ± 19 |

*p < 0.001

Increase of the [$^3$H]paf binding at the concentrations of paf and lyso-paf as shown, but not paf enantiomer and lyso phosphatidylcholine (LPC). Lyso paf increased the binding of [$^3$H]paf (3.25 nM, 20° C., 30 min) per 2.5×10⁶ PMN reaching a plateau at 5 nM. Web 2086 (1 μM) inhibited the increased total [$^3$H]paf binding. Values are means±1 S.E.M. of six experiments and lyso paf effects were significant using the "Student's t test for paired samples". Table 1 shows that paf and lyso paf upregulates the paf receptor on human neutrophils in a significant and specific manner.

TABLE 2

Effect of paf in comparison with PMA on the [³H]paf binding.

| Preincubation (min at 37° C.) | none | paf (5 nM) | paf + WEB 2086 | PMA (nM) 1 | PMA (nM) 16 |
|---|---|---|---|---|---|
| 0 | 354 | 414 | 274 | 385 | 219 |
| 15 | 342 | 331 | 226 | 413 | 171 |

Dual effects of paf and PMA were similar to that of paf when the compounds were added simultaneously with [³H]paf (3.25 nM, 30 min, 20° C.) Low dose paf failed to increase [³H]paf binding after 15 min preincubation, whereas the dual effect of PMA was enhanced. Results are expressed in fmol [³H]paf bound per $2.5 \times 10^6$ PMN and are representative of 6 experiments. Table 2 shows that the upregulation of paf receptors is mediated by the protein kinase C.

TABLE 3

Metabolism of [³H]paf in PMN.

| Addition | paf | lyso paf | alkyl-acyl-GPC |
|---|---|---|---|
| vehicles | 80.0 ± 10.8 | 1.3 ± 1.2 | 8.1 ± 11.6 |
| paf (5 nM) | 78.9 ± 11.3 | 0.8 ± 0.8 | 22.1 ± 11.9 |
| WEB 2086 | 82.3 ± 8.0 | 0.5 ± 0.8 | 16.7 ± 8.5 |

PMN ($2.5 \times 10^6$) metabolized added [³H]paf to [³H]alkyl-acyl-GPC and [³H]lyso paf as an intermediary. PMN were incubated with [³H]paf under functionally relevant binding conditions (6.5 nM, 30 min at 20° C.) before they were separated by filtration. PMN-bound phospholipids on the filters were extracted and purified by HPLC. Values are expressed as a percentage of radioactivity recovered in all fractions after subtraction of the background values. They are means±1 s.d. from 3 experiments. FIG. 3 shows the metabolism of paf by intact human neutrophils.

I claim:

1. A method of treating psychosis or paranoid syndrome with elevated lyso paf levels comprising administering to a subject requiring said treatment an effective amount of at least one triazolothieno-diazepine selected from the group consisting of 3-(4-(2-chlorophenyl)-9-methyl-6H-thieno (3,2-f)(1,2,4) triazolo-(4,3-a)-(1,4) diazepine-2-yl)-1-(4-morpholinyl)-1-propanone; (3-(4-(2-chlorophenyl)- 9-cyclopropyl-6H-thieno (3,2-f)-(1,2,4) triazolo (4,3-a) (1,4) diazepine-2-yl)-1-(4-morpholinyl)-1-propanone; and tetrahydro-4,7,8,10 methyl (chloro-2 phenyl)6 (dimethoxy-3,4-phenyl) thio) methylthiocarbonyl-9 pyrido (4',3', −4.5) thieno (3,2-f) triazolo-1,2,3(4,3-a) diazepine-1.4).

* * * * *

UNITED STATES PATENT AND TRADEMARK OFFICE
CERTIFICATE OF CORRECTION

PATENT NO. : 5,346,894
DATED : September 13, 1994
INVENTOR(S) : Ruth KORTH

It is certified that error appears in the above-identified patent and that said Letters Patent is hereby corrected as shown below:

In Column 12, Claim One, Line 25, change "triazolo-1,2,3,(4,3-a) diazepine-1.4)" to -- triazolo-1,2,4(4,3-a) diazepine-1,4) --.

Signed and Sealed this

Third Day of January, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,346,894　　　　　　　　　　　Page 1 of 3
DATED : September 13, 1994
INVENTOR(S) : Ruth KORTH It is certified that error appears in the above-identified patent and that said Letters Patent is hereby corrected as shown below:

Column 1, line 35, after "paf" insert -- via --.

Column 1, line 61, delete "or" and insert therefor -- of --.

Column 1, line 62, after "Thus" insert -- , --.

Column 2, line 1, delete "of" and insert therefor -- or --.

Column 2, line 2, delete "attach" and insert therefor -- attack --.

Column 2, line 12, delete "520202" and insert therefor -- 52020 --.

Column 2, line 39, begin a new paragraph with -- The paf antagonist --.

Column 2, line 39 delete "tropically" and insert therefor -- topically --.

Column 7, line 11, delete "37 C" and insert therefor -- 37° C --.

UNITED STATES PATENT AND TRADEMARK OFFICE
CERTIFICATE OF CORRECTION

PATENT NO. : 5,346,894
DATED : September 13, 1994
INVENTOR(S) : Ruth KORTH

It is certified that error appears in the above-identified patent and that said Letters Patent is hereby corrected as shown below:

Column 8, line 26, delete "4° C." and insert therefor -- 4° C the --.

Column 8, line 37, delete "N=6" and insert therefor -- n=6 --.

Column 8, line 38, delete "Table" and insert therefor -- table --.

Column 8, line 49, delete "either" and insert therefor -- ether --.

UNITED STATES PATENT AND TRADEMARK OFFICE
CERTIFICATE OF CORRECTION

PATENT NO. : 5,346,894
DATED : September 13, 1994
INVENTOR(S) : Ruth KORTH

It is certified that error appears in the above-indentified patent and that said Letters Patent is hereby corrected as shown below:

Column 10, line 17, delete "(B,■)" and insert therefor -- (B,▲) --.

Column 10, line 30, delete "(500 nM,☐) and insert therefor -- (500 nM,▲) --.

Signed and Sealed this

Twenty-eighth Day of May, 1996

Attest:

BRUCE LEHMAN

Attesting Officer     Commissioner of Patents and Trademarks